United States Patent
Carroll et al.

(10) Patent No.: US 12,270,743 B2
(45) Date of Patent: Apr. 8, 2025

(54) SYSTEM AND METHOD FOR VAPORISING LIQUIFIED NATURAL GAS FOR MEASUREMENT THEREOF

(71) Applicant: SYNERTEC PTY LTD, Camberwell (AU)

(72) Inventors: Michael James Carroll, Hawthorn East (AU); Sandra Mercedes Neira Sanchez, Box Hill (AU); Christopher Borg, Wildwood (AU); Lee Matthew Morony, Melbourne (AU)

(73) Assignee: SYNERTEC PTY LTD, Camberwell (AU)

( * ) Notice: Subject to any disclaimer, the term of this patent is extended or adjusted under 35 U.S.C. 154(b) by 241 days.

(21) Appl. No.: 17/780,784

(22) PCT Filed: Nov. 27, 2020

(86) PCT No.: PCT/AU2020/051290
§ 371 (c)(1),
(2) Date: May 27, 2022

(87) PCT Pub. No.: WO2021/102522
PCT Pub. Date: Jun. 3, 2021

(65) Prior Publication Data
US 2022/0412852 A1    Dec. 29, 2022

(30) Foreign Application Priority Data
Nov. 27, 2019   (AU) ................................ 2019904471

(51) Int. Cl.
*G01N 1/44* (2006.01)
*F17D 3/10* (2006.01)
(Continued)

(52) U.S. Cl.
CPC ................. *G01N 1/44* (2013.01); *F17D 3/10* (2013.01); *F17D 5/00* (2013.01); *G01N 33/28* (2013.01)

(58) Field of Classification Search
CPC .. G01N 1/44; G01N 33/28; F17D 3/10; F17D 5/00
See application file for complete search history.

(56) References Cited

U.S. PATENT DOCUMENTS 3,487,692 A * 1/1970 Cook, Jr. ................. G01N 1/10
73/864.91
10,126,214 B1 * 11/2018 St Amant, III ...... G01N 1/4022

FOREIGN PATENT DOCUMENTS

CN          108152428 A  *  6/2018

OTHER PUBLICATIONS

International Search Report in related PCT Application No. PCT/AU2020/051290 dated Feb. 19, 2021.

* cited by examiner

*Primary Examiner* — Jamel E Williams
(74) *Attorney, Agent, or Firm* — Mark Malek; Widerman Malek, PL

(57) ABSTRACT

A method of vaporising liquefied natural gas (LNG) for measurement of its constituent components may include receiving LNG from a main pipeline into a pressurising device. The method may also include via the pressurising device, pressurising a the LNG beyond a critical pressure thereof. The method may further include directing a first portion of the pressurised LNG to a heater. The method may still further include via the heater, heating the first portion of pressurised LNG beyond a critical temperature thereof, and directing the pressurised and heated LNG to a vaporising device. The method may also include via the vaporising (Continued)

device, depressurising the heated LNG to a pressure below the critical pressure so as to vaporise the LNG.

18 Claims, 6 Drawing Sheets

(51) Int. Cl.
*F17D 5/00* (2006.01)
*G01N 33/28* (2006.01)

SYSTEM AND METHOD FOR VAPORISING LIQUIFIED NATURAL GAS FOR MEASUREMENT THEREOF

RELATED APPLICATIONS

This application is a national phase application of and claims priority under 35 U.S.C. § 371 of PCT Application No. PCT/AU2020/051290 filed on Nov. 27, 2020 and titled SYSTEM AND METHOD FOR VAPORISING LIQUIFIED NATURAL GAS FOR MEASUREMENT THEREOF, which claims the benefit of AU 2019904471, filed on Nov. 27, 2019, each of which is hereby incorporated by reference in its entirety.

FIELD OF THE INVENTION

The present invention relates to a system and method for vaporising liquefied natural gas (LNG) for sampling. In particular, the invention relates to a system and method for vaporising a sample of an LNG shipment so that the composition of the sample, and thus the shipment, can be accurately determined.

BACKGROUND

LNG is typically sold based on its British thermal unit (BTU) value. As such, it is crucial for suppliers and purchasers of LNG that the BTU value of any LNG shipment is accurately known, as well as the constituent components thereof.

To estimate the expected selling price of a particular LNG shipment, a supplier may determine the BTU value of that shipment as it is loaded onto a tanker ship. A complication is that the BTU value of an LNG shipment is likely to change during transit (e.g. due to vaporisation) and thus may not be the same once the shipment reaches the purchaser. As such, the purchaser of the LNG shipment may also want to determine the BTU value of the LNG shipment as it is off-loaded from the tanker ship to avoid overpaying for the LNG shipment. The operator of the tanker ship may also be interested in any changes in BTU value, not least because they often burn LNG that vaporises during transit and are thus financially liable for the amount burned.

Known methods for estimating the BTU value and constituent components of LNG involve taking samples, often intermittently or continuously, from the shipment as it is off-loaded from the tanker ship. At least a portion of those samples is then vaporised and analysed to determine the BTU value and constituent components of the sample in order to deduce these properties of the LNG shipment. However, such methods are not sufficiently accurate.

One reason for inaccuracy results from the fact that LNG is made from a range of different hydrocarbon compounds, each with different properties such as different boiling points. As such, under certain pressures and temperatures, LNG is vulnerable to fractionation, whereby components thereof exist in different phases (i.e. in liquid and gaseous phases). Inaccuracies can thus arise if a portion of the LNG sample being tested, by gas chromatography for example, vaporises prior to the actual vaporisation stage of a sampling system.

Common approaches which attempt to avoid premature partial vaporisation of LNG samples involve using lines and pipes which are as short as possible, with diameters as small as possible, and thermally insulating them to help maintain LNG samples in a sub-cooled state before arriving at a vaporiser. However, such approaches are not sufficiently reliable for maintaining LNG samples in a sub-cooled state, rendering the LNG samples vulnerable to partial vaporisation before the vaporisation stage.

Another common approach involves vaporising the LNG sample through rapid heating of the sample in the vaporiser. This process intends to heat the sample of LNG, which is in an all-liquid phase, to an all-gas phase instantaneously. However, the process of heating the LNG sample is typically not immediate and therefore the sample transitions through a mixed liquid and gas phase while this process is carried out. This approach causes fractionation of the sample.

These approaches typically give rise to test results that do not accurately reflect the composition of the LNG sample, and thus do not accurately reflect the composition of the LNG shipment from which the LNG sample was taken.

Considering that an LNG shipment can be worth tens of millions of dollars, even minor uncertainties and inaccuracies in the measurement of LNG samples can have a large impact on the price of the LNG shipment, and the resulting profitability of LNG suppliers, purchasers, distributors and end-consumers.

There is a need to address the above, and/or at least provide a useful alternative.

SUMMARY

According to a first aspect of the present invention, there is provided a method of vaporising liquified natural gas (LNG) for measurement of its constituent components, the method comprising:
  receiving LNG from a main pipeline into a pressurising device;
  via the pressurising device, pressurising the LNG beyond a critical pressure thereof;
  directing a first portion of the pressurised LNG to a heater;
  via the heater, heating the first portion of pressurised LNG beyond a critical temperature thereof;
  directing the pressurised and heated LNG to a vaporising device; and
  via the vaporising device, depressurising the heated LNG to a pressure below the critical pressure so as to vaporise the LNG.

In embodiments of the invention, the vaporising device comprises a regulator and the pressurised and heated LNG is depressurised as it exits the regulator.

In embodiments of the invention, the regulator comprises a pressure control valve.

In embodiments of the invention, the method further comprises directing the vaporised LNG to a downstream measurement system configured to measure the constituent components of the vaporised LNG.

In embodiments of the invention, the method further comprises directing the vaporised LNG to a downstream device to collect representative samples of the LNG.

In embodiments of the invention, the step of receiving the LNG into the pressurising device comprises receiving the LNG at a temperature and pressure below the critical temperature and critical pressure, respectively.

In embodiments of the invention, the step of receiving the LNG into the pressuring device comprises receiving the LNG at a temperature of approximately −160° C. and a pressure of approximately 1 to 4 Barg.

In embodiments of the invention, the step of pressurising the LNG comprises pressurising the LNG to approximately 80 Barg such that the pressure of the LNG exceeds the critical pressure thereof.

In embodiments of the invention, the step of heating the first portion of LNG comprises heating the first portion of LNG to a temperature between approximately −10° C. and approximately 45° C. such that the temperature of the LNG exceeds the critical temperature thereof.

In embodiments of the invention, the step of depressurising the first portion of LNG comprises reducing the pressure to approximately 4 Barg such that the pressure of the first portion of LNG is below the critical pressure, thereby vaporising the LNG.

In embodiments of the invention, the method further comprises returning a second portion of the pressurised LNG from the pressurising device to the main pipeline.

In embodiments of the invention, the method further comprises returning vaporised LNG from the pressurising device to the main pipeline.

In embodiments of the invention, the method further comprises:
  checking that the LNG has been pressurised beyond the critical pressure before directing the first portion of the LNG to the heater; and
  returning the LNG to the main pipeline if LNG outputted from the pressurising device is not above the critical pressure.

In embodiments of the invention, the method further comprises priming the pressurising device with LNG received from the main pipeline and returning said LNG to the main pipeline.

According to a second aspect of the present invention, there is provided a system for vaporising LNG for measurement of its constituent components, the system comprising:
  a pressurising device for receiving from a main pipeline LNG to be measured, the pressurising device being configured to pressurise the LNG beyond a critical pressure thereof;
  a heater for heating a first portion of the pressurised LNG from the pressurising device above a critical temperature thereof; and
  a vaporising device for depressurising the pressurised and heated LNG from the heater to a pressure below the critical pressure so as to vaporise the LNG.

In embodiments of the invention, the vaporising device comprises a regulator configured such that the LNG is depressurised to a pressure below the critical pressure as it exits the regulator.

In embodiments of the invention, the regulator comprises a pressure control valve.

In embodiments of the invention, the system further comprises a downstream measurement system configured to measure the constituent components of the vaporised LNG.

In embodiments of the invention, the system further comprises a downstream device configured to collect representative vaporised samples of the LNG to be measured.

In embodiments of the invention, the pressurising device is configured to receive the LNG at a temperature and pressure below the critical temperature and critical pressure, respectively.

In embodiments of the invention, the pressurising device is configured to receive the LNG at a temperature of approximately −160° C. and a pressure of approximately 1 to 4 Barg.

In embodiments of the invention, the pressurising device is configured to pressurise the LNG to approximately 80 Barg such that the pressure of the LNG exceeds the critical pressure thereof.

In embodiments of the invention, the heater is configured to heat the first portion of the pressurised LNG to a temperature between approximately −10° C. and approximately 45° C. such that the temperature of the first portion of LNG exceeds the critical temperature thereof.

In embodiments of the invention, the vaporising device is configured to reduce the pressure of the first portion of LNG outputted from the heater to approximately 4 Barg such that the first portion of LNG is below the critical pressure thereof, thereby vaporising the LNG.

In embodiments of the invention, the system is configured to return a second portion of the pressurised LNG from the pressurising device to the main pipeline.

In embodiments of the invention, the system is configured to return vaporised LNG from the pressurising device to the main pipeline.

In embodiments of the invention, the system further comprises a pressure control system configured to:
  monitor the pressure of the LNG outputted from the pressurising device;
  if the pressure of the outputted LNG is below the critical pressure, return the LNG outputted from the pressurising device to the main pipeline; and
  if the pressure of the outputted LNG is above the critical pressure, direct the first portion of LNG outputted from the pressurising device to the heater and return a second portion of the LNG outputted from the pressurising device to the main pipeline.

In embodiments of the invention, the system is configured such that the pressurising device is primed by LNG drawn from the main pipeline, which LNG is then returned thereto.

BRIEF DESCRIPTION OF THE DRAWINGS

In order that the invention may be more easily understood, an embodiment will now be described, by way of example only, with reference to the accompanying drawings.

DETAILED DESCRIPTION

Figure 4:
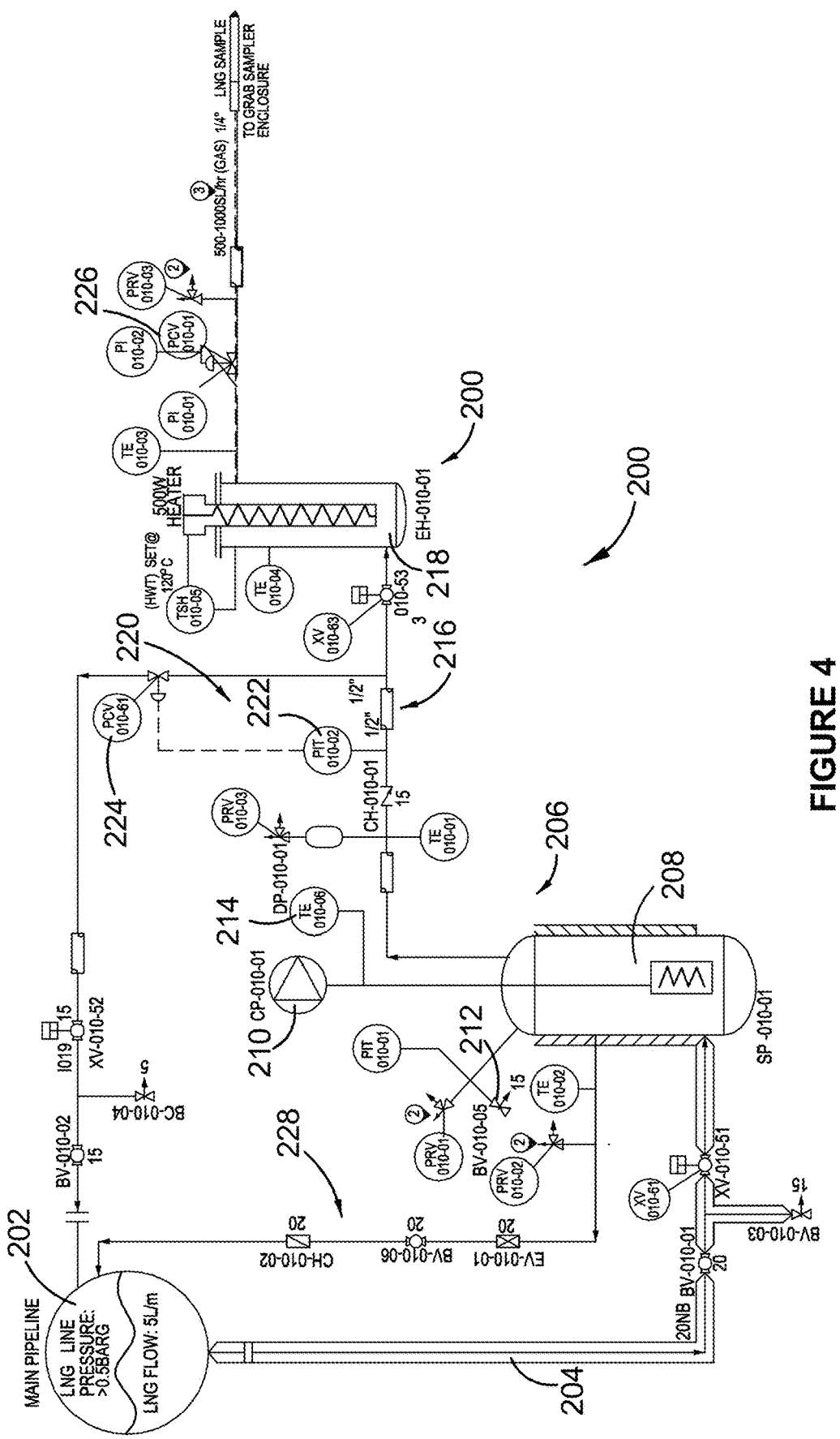
FIG. 4 is a P&ID of a system embodying the invention.
Figure 5:
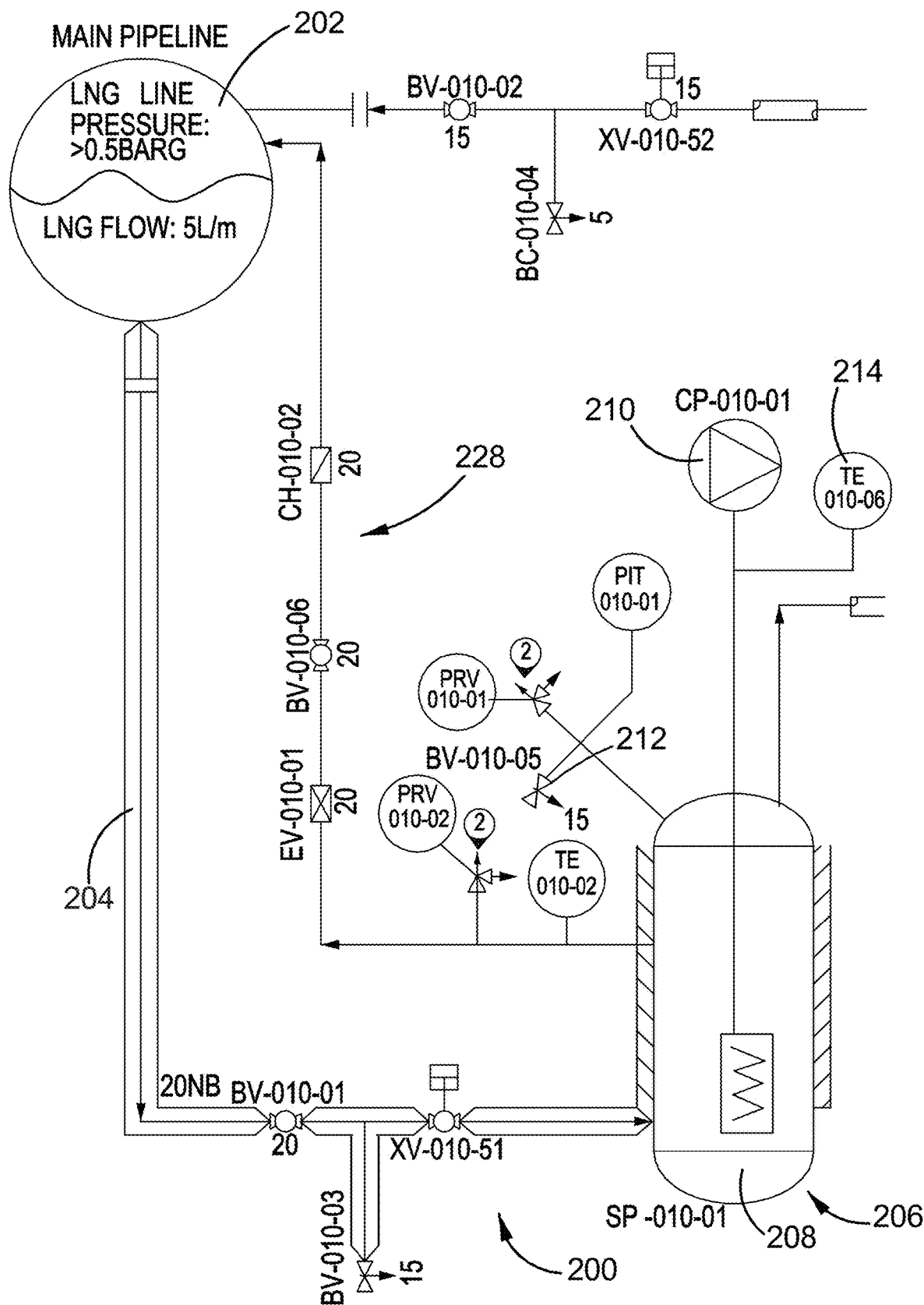
FIG. 5 a close-up view of a left-hand side of the P&ID of FIG. 4.
Figure 6:
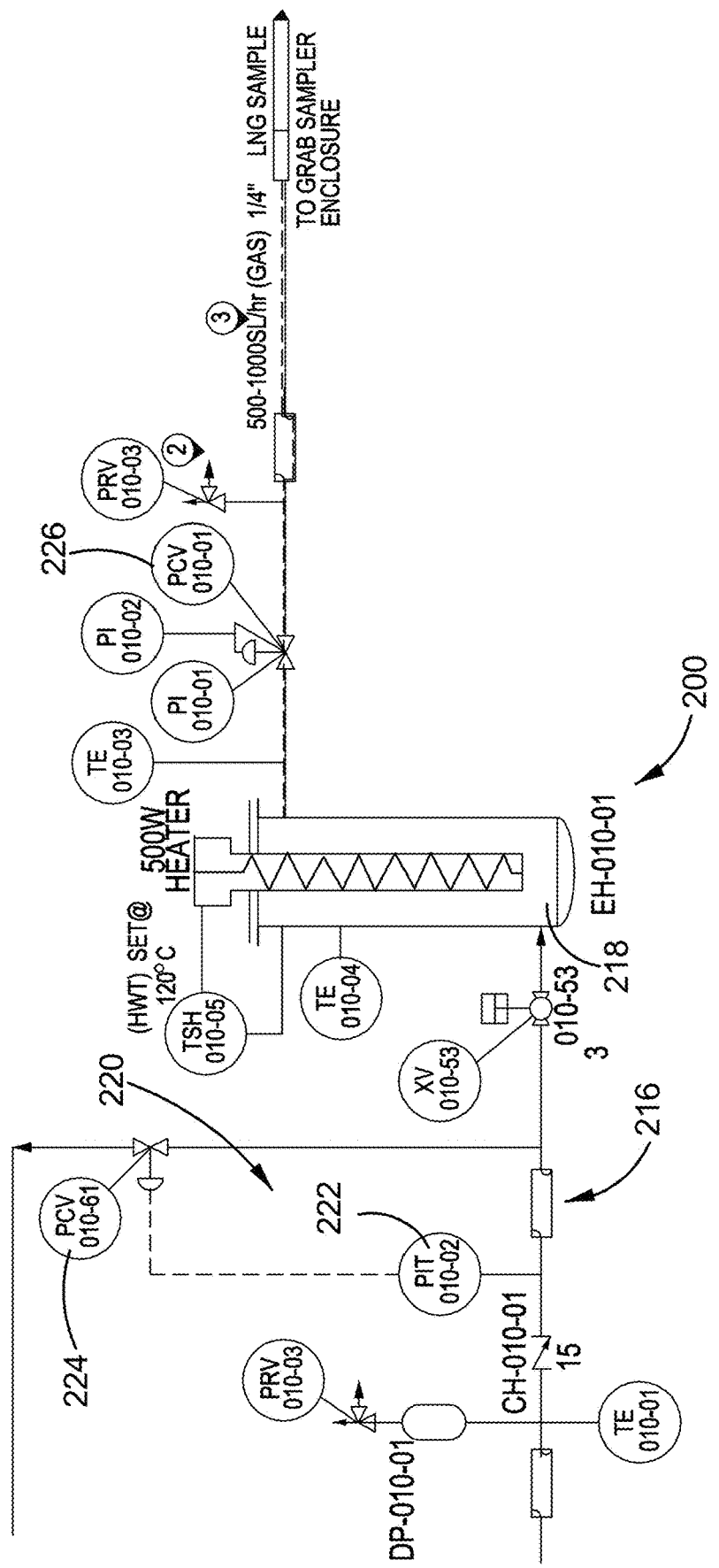
FIG. 6 is a close-up view of a right-hand side of the P&ID of FIG. 4.

FIGS. 1 to 6 are piping and instrumentation diagrams (P&ID) which illustrate an embodiment of the present system 200 and method. The P&IDs have been prepared in accordance with standardized P&ID symbols and notations, as detailed in standards such as ISA S5.1, ISO 10628 and ISO 14617. The P&IDs of FIGS. 4 to 6 are modified versions of the P&IDs of FIGS. 1 to 3, respectively, to include reference numerals.

In the depicted embodiment, LNG is drawn from a main pipeline 202 and directed through a vacuum insulated hose 204 to a pressurising device 206. In the Figures, the pressurising device 206 comprises a vacuum insulated sump pump 208 and a pump, such as a cryogenic pump 210.

Advantageously, LNG is extracted from the main pipeline 202 at a sufficient velocity and static pressure (approximately 1 to 4 Barg) such that the energy of the LNG can be utilised to prime the cryogenic pump 210. Connected to the cryogenic pump 210 is valve 212 which can be intermittently opened to vent off any vapor trapped in the cryogenic pump 210, thereby aiding the priming process. LNG used to prime the pressurising device 206 is recirculated back to the main pipeline 202. In alternate embodiments of the invention, the LNG may be recirculated back to the main pipeline 202 via an eductor (not shown).

Once the cryogenic pump 210 has been primed, the LNG is pressurized by the cryogenic pump 210. The cryogenic pump 210 is configured to pressurise the LNG beyond its critical pressure, preferably to a pressure of approximately 80 Barg. It is envisaged that the pressurisation occurs at a relatively stable and controlled temperature. To this end, temperature element 214 is configured to monitor a seal temperature, wherein if the seal temperature drops below the ambient temperature, it indicates that an LNG leak is present and provides a signal to shut down the system 200.

After the LNG has been pressurised by the cryogenic pump 210 to a pressure above the critical pressure, at least a first portion of the LNG is outputted through an insulated pipeline 216 toward a heater 218. A second portion of the pressurised LNG, typically a substantially larger portion, is returned to the main pipeline via pathway 228 of the system 200. As such, as the system 200 is running, pressurised LNG outputted from the pressurising device 206 continuously recirculates back to the main pipeline 202.

Before the first portion of pressurised LNG enters the heater 218, it is important to ensure that the pressurised LNG has not suffered any pressure losses and is still at the desired pressure of approximately 80 Barg, or at least above the critical pressure. To this end, there is a pressure control loop 220 downstream of the cryogenic pump 210 and upstream of the heater 218. The control loop 220 comprises a pressure indicating transmitter 222 which monitors the pressure of the LNG outputted from the cryogenic pump 210 and is in communication with pressure control valve 224. The pressure control valve 224 opens and closes based on the pressure reading from the pressure indicating transmitter 222 to ensure that the LNG entering the heater 218 is at or above the minimum desired pressure of 80 Barg. If the pressure of the LNG is too low, the pressure control valve 224 closes to allow the pressure of the LNG to increase to the desired pressure. If the LNG is above the desired pressure, the pressure control valve 224 is configured to open, allowing LNG to flow to the main pipeline 202 to maintain the pressure at the desired pressure and avoid overpressurization in the system 200. As such, the pressure control loop 220 ensures that only LNG that is above its critical pressure enters the heater 218. In this way, there is little-to-no risk that any pressurised LNG in the heater 218 will undergo fractionation before heating therein.

The LNG is regulated as it enters the heater 218 via an adjustable restriction orifice and a capillary. Heat is applied to the pressurised LNG within the heater 218 so as to heat the LNG sample above the critical temperature. As such, the LNG outputted from the heater 218 has been pressurised above the critical pressure and heated above the critical temperature without the LNG entering a mixed liquid and gas phase. The heated and pressurised LNG is thus ready for rapid vaporisation by reducing its pressure below the critical pressure, as discussed below.

The heated and pressurised LNG is outputted from the heater 218 to a vaporising device 226 via which the LNG can be depressurised to a pressure below the critical pressure such that the LNG is rapidly vaporised. The term 'vaporising device' should be understood as referring to any one or more devices of the system 200 configured to bring about a depressurisation of the LNG outputted from the heater 218.

In the depicted embodiment, the vaporising device comprises a regulator, shown in the form of a pressure control valve 226 of the system 200. As the LNG exits the pressure control valve 226, the pressure of the LNG is reduced below the critical pressure to approximately 4 Barg, thereby vaporising the LNG. Advantageously, this lower pressure is suitable for downstream systems and devices used for measuring the constituent components of the vaporised LNG. Because the LNG has been pressurised beyond its critical pressure and heated above its critical temperature before being vaporised, the LNG is not vulnerable to fractionation during the vaporisation process. As such, the resulting vapor gas constitutes a sample whose composition accurately reflects the composition of the LNG shipment. As such, downstream measurement and analysis of the vapor gas sample provide accurate composition information of the LNG shipment.

Figure 1:
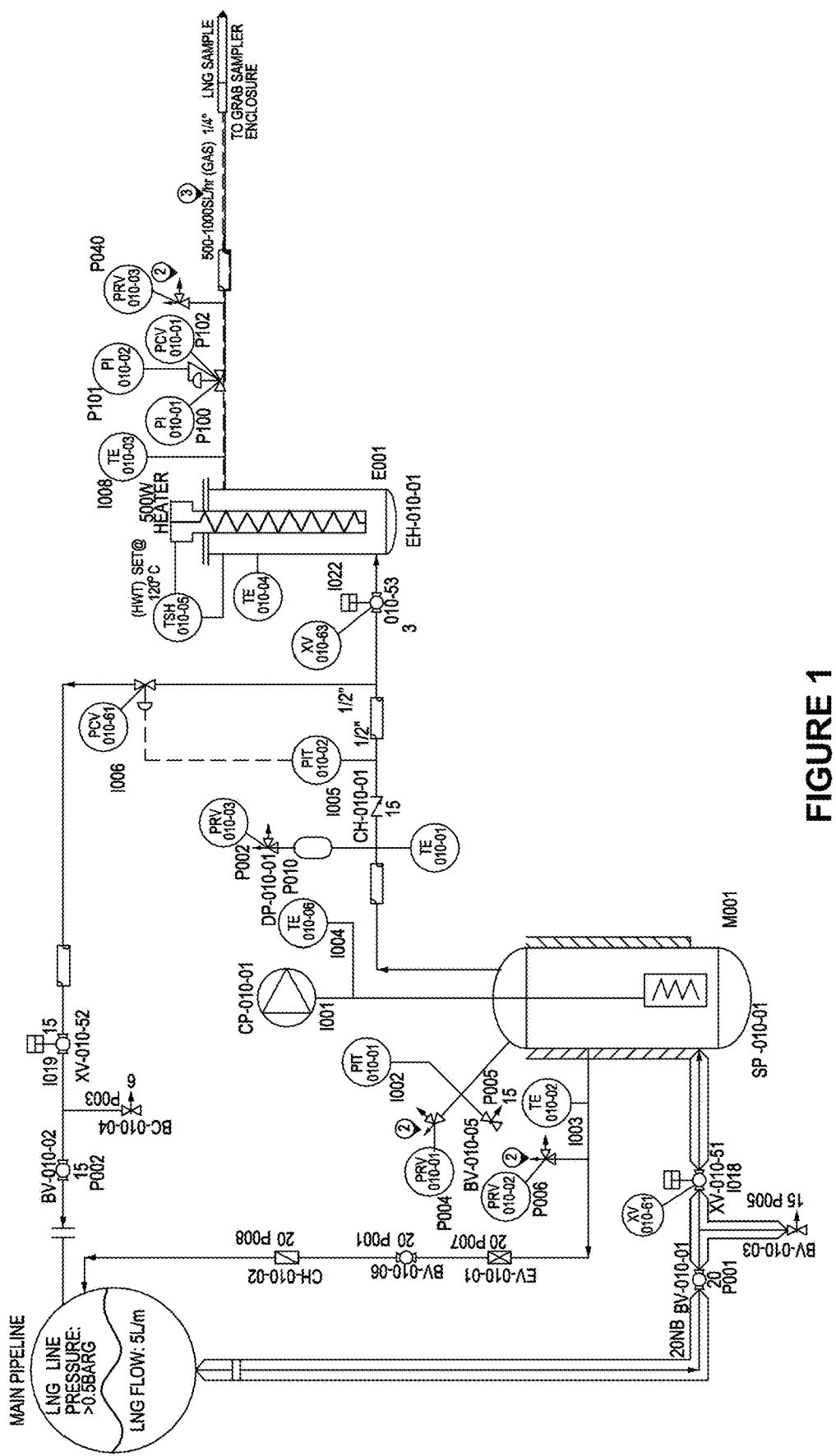
FIG. 1 is a piping and instrumentation diagram (P&ID) of a system embodying the invention.
Figure 2:
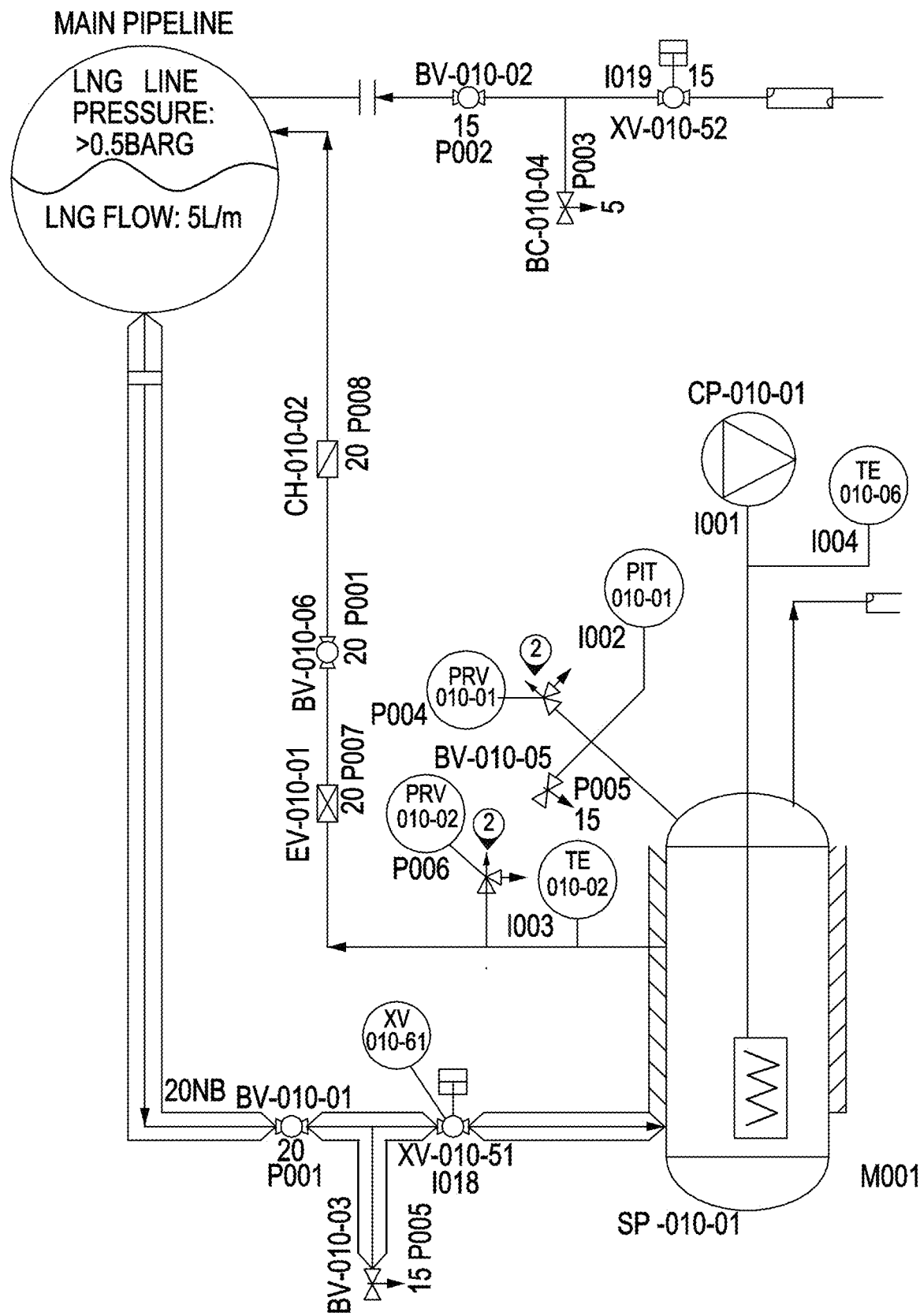
FIG. 2 a close-up view of a left-hand side of the P&ID of FIG. 1.
Figure 3:
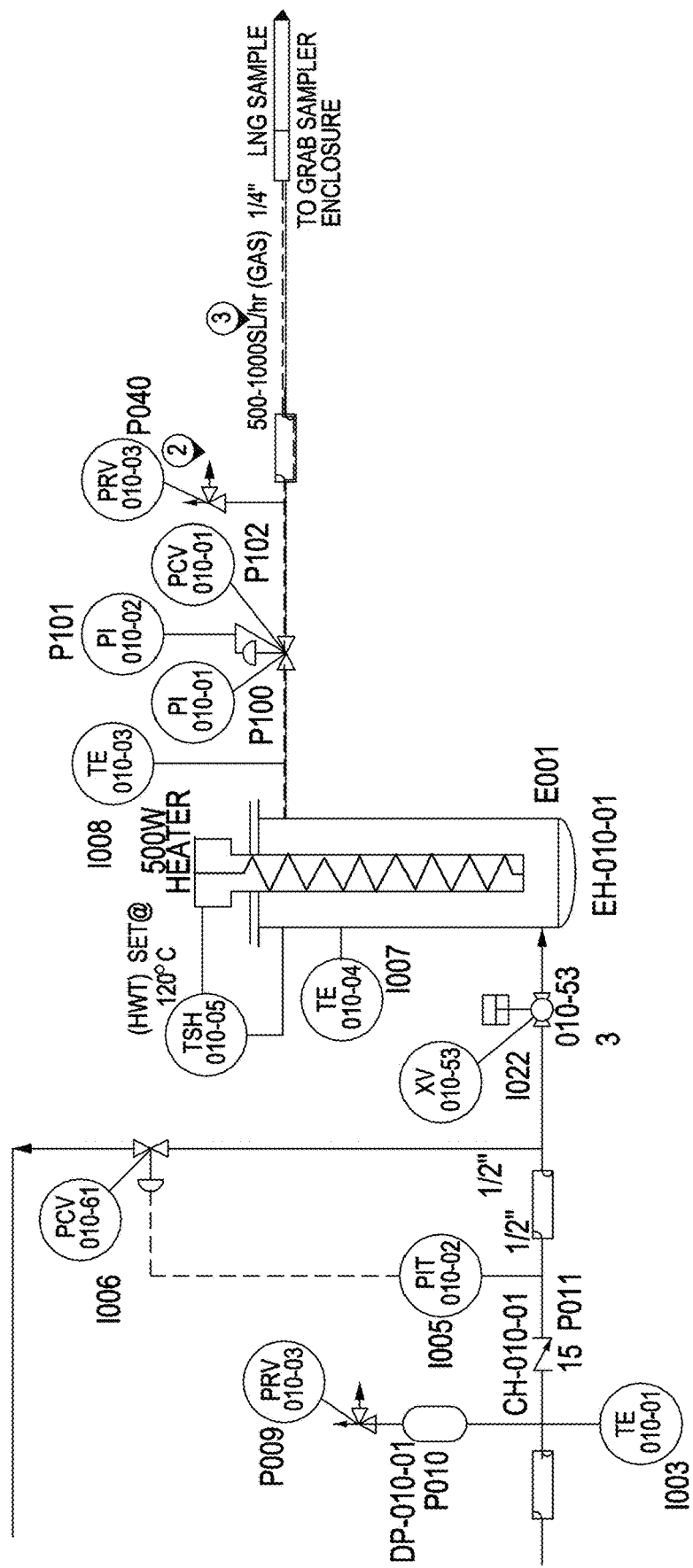
FIG. 3 is a close-up view of a right-hand side of the P&ID of FIG. 1.

With reference to FIG. 1, it is generally preferable to position the pressurising device 206 proximate to the main pipeline 202 to minimise pressure losses that might occur when transferring LNG to the cryogenic pump 210; pressure losses can result in inadvertent boiling of the LNG before it reaches the pressurising device 206. Additional measures, such as reducing the length and/or diameter of interconnecting piping and incorporating impact probes may assist with reducing pressure losses.

Advantageously, once the LNG has been pressurised beyond its critical pressure, the pressurised LNG is less vulnerable to boiling or fractionation; as such, downstream components in the system 200, such as the heater 218 and vaporising device 226 etc. may be positioned relatively more remotely from the LNG main pipeline 202 and/or in more customised arrangements as needed. As such, the present system 200 can be better adapted to suit different site and/or ship configurations and layouts.

Many modifications of the above embodiments will be apparent to those skilled in the art without departing from the scope of the present invention. For example, the pressures and temperatures described may be varied as necessary, provided that the pressurising device 206 pressurises the LNG beyond its critical pressure, and the heater 218 heats the pressurised LNG beyond its critical temperature. Similarly, the specific components and placements thereof in the Figures are merely exemplary and can be varied without departing from the scope of the invention to achieve the vaporisation of LNG with little to no possibility of inadvertent fractionation during vaporisation.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

PARTS LIST

The P&IDs incorporate item labels, tag numbers and reference numerals to refer to instruments, devices and other features of embodiments of the present invention, as summarised in the below table:

| Item label | Description | Tag number | Reference numeral |
|---|---|---|---|
|  | SYSTEM |  | 200 |
|  | MAIN PIPELINE |  | 202 |
|  | INSULATED HOSE |  | 204 |
|  | PRESSURISING DEVICE |  | 206 |
|  | INSULATED PIPELINE |  | 216 |
|  | PRESSURE CONTROL LOOP |  | 220 |
|  | PATHWAY |  | 228 |
| E001 | HEATER | EH-010-01 | 218 |
| I001 | CRYOGENIC PUMP | CP-010-01 | 210 |
| I002 | PRESSURE TRANSMITTER | PIT-010-01 |  |
| I003 | TEMPERATURE ELEMENT | TE-010-01 |  |
| I004 | TEMPERATURE ELEMENT | TE-010-06 | 214 |
| I005 | PRESSURE TRANSMITTER | PIT-010-02 | 222 |
| I006 | PRESSURE CONTROL VALVE | PCV-010-51 | 224 |
| I007 | TEMPERATURE ELEMENT | TE-010-04 |  |
| I008 | TEMPERATURE ELEMENT | TE-010-03 |  |
| I018 | PNEUMATIC ISOLATION VALVE (2-WAY) | XV-010-51 |  |
| I019 | PNEUMATIC ISOLATION VALVE (2-WAY) | XV-010-52 |  |
| I022 | PNEUMATIC ISOLATION VALVE (2-WAY) | XV-010-53 |  |
| M001 | PUMP SUMP | SP-010-01 | 208 |
| P001 | ISOLATION BALL VALVE (2-WAY) | BV-010-01, BV-010-06 |  |
| P002 | ISOLATION BALL VALVE (2-WAY) | BV-010-02 |  |
| P003 | NEEDLE VALVE | BV-010-04 |  |
| P004 | PRESSURE RELIEF VALVE | PRV-010-01 |  |
| P005 | NEEDLE VALVE | BV-010-03, BV-010-05 | 212 |
| P006 | RELIEF VALVE | PRV-010-02 |  |
| P007 | EXPANSION VALVE | EV-010-01 |  |
| P008 | CHECK VALVE | CH-010-02 |  |
| P009 | RELIEF VALVE | PRV-010-03 |  |
| P010 | PULSATION DAMPER | DP-010-01 |  |
| P011 | CHECK VALVE | CH-010-01 |  |
| P040 | PRESSURE RELIEF VALVE | PRV-010-03 |  |
| P100 | PRESSURE GAUGE | PI-010-01 |  |
| P101 | PRESSURE GAUGE | PI-010-02 |  |
| P102 | VAPORISER (PRESSURE CONTROL VALVE) | PCV-010-01 | 226 |

The invention claimed is:

1. A method of vaporising liquified natural gas (LNG) for measurement of its constituent components, the method comprising:
   receiving LNG from a main pipeline into a pressurising device;
   via the pressurising device, pressurising the LNG beyond a critical pressure thereof;
   directing a first portion of the pressurised LNG to a heater;
   via the heater, heating the first portion of pressurised LNG beyond a critical temperature thereof;
   directing the pressurised and heated LNG to a vaporising device;
   via the vaporising device, depressurising the heated LNG to a pressure below the critical pressure so as to vaporise the LNG; and
   returning a second portion of the pressurised LNG from the pressurising device to the main pipeline.

2. The method according to claim 1, wherein the vaporising device comprises a regulator and the pressurised and heated LNG is depressurised as it exits the regulator.

3. The method according claim 1, further comprising directing the vaporised LNG to a downstream measurement system configured to measure the constituent components of the vaporised LNG.

4. The method according to claim 1, wherein the step of pressurising the LNG comprises pressurising the LNG to approximately 80 Barg such that the pressure of the LNG exceeds the critical pressure thereof.

5. The method according to claim 1, wherein the step of heating the first portion of LNG comprises heating the first portion of LNG to a temperature between approximately −10° C. and approximately 45° C. such that the temperature of the LNG exceeds the critical temperature thereof.

6. The method according to claim 1, wherein the step of depressurising the first portion of LNG comprises reducing the pressure to approximately 4 Barg such that the pressure of the first portion of LNG is below the critical pressure, thereby vaporising the LNG.

7. The method according to claim 1, further comprising returning vaporised LNG from the pressurising device to the main pipeline.

8. The method according to claim 1, further comprising:
   checking that the LNG has been pressurised beyond the critical pressure before directing the first portion of the LNG to the heater; and returning the LNG to the main pipeline if LNG outputted from the pressurising device is not above the critical pressure.

9. The method according to claim 1, further comprising priming the pressurising device with LNG received from the main pipeline and returning said LNG to the main pipeline.

10. A system for vaporising LNG for measurement of its constituent components, the system comprising:
    a pressurising device for receiving from a main pipeline LNG to be measured, the pressurising device being configured to pressurise the LNG beyond a critical pressure thereof;
    a heater for heating a first portion of the pressurised LNG from the pressurising device above a critical temperature thereof; and
    a vaporising device for depressurising the pressurised and heated LNG from the heater to a pressure below the critical pressure so as to vaporise the LNG;
    wherein a second portion of the pressurised LNG is returned from the pressurising device to the main pipeline.

11. The system according to claim 10, wherein the vaporising device comprises a regulator configured such that the LNG is depressurised to a pressure below the critical pressure as it exits the regulator.

12. The system according to claim 10, further comprising a downstream measurement system configured to measure the constituent components of the vaporised LNG.

13. The system according to claim 10, wherein the pressurising device is configured to pressurise the LNG to approximately 80 Barg such that the pressure of the LNG exceeds the critical pressure thereof.

14. The system according to claim 10, wherein the heater is configured to heat the first portion of the pressurised LNG to a temperature between approximately −10° C. and approximately 45° C. such that the temperature of the first portion of LNG exceeds the critical temperature thereof.

15. The system according to claim 10, wherein the vaporising device is configured to reduce the pressure of the first portion of LNG outputted from the heater to approximately 4 Barg such that the first portion of LNG is below the critical pressure thereof, thereby vaporising the LNG.

16. The system according to claim 10, wherein the system is configured to return vaporised LNG from the pressurising device to the main pipeline.

17. The system according to claim 10, further comprising a pressure control system configured to: monitor the pressure of the LNG outputted from the pressurising device; if the pressure of the outputted LNG is below the critical pressure, return the LNG outputted from the pressurising device to the main pipeline; and if the pressure of the outputted LNG is above the critical pressure, direct the first portion of LNG outputted from the pressurising device to the heater and return a second portion of the LNG outputted from the pressurising device to the main pipeline.

18. The system according to claim 10, configured such that the pressurising device is primed by LNG drawn from the main pipeline, which LNG is then returned thereto.

* * * * *